United States Patent [19]

Gilles

[11] Patent Number: 4,728,326

[45] Date of Patent: Mar. 1, 1988

[54] ADJUSTABLE DIAPER

[76] Inventor: Jennifer A. Gilles, 10591 Bridgeport, Richmond, B.C., Canada, V6X 1S9

[21] Appl. No.: 815,740

[22] Filed: Jan. 2, 1986

[51] Int. Cl.$^4$ .............................................. A61F 13/16
[52] U.S. Cl. .................................... 604/391; 604/392; 604/385 R; 128/DIG. 15
[58] Field of Search ................... 604/358, 385.1, 385.2, 604/386, 387, 391, 392, 394; 128/DIG. 15

[56] References Cited

U.S. PATENT DOCUMENTS

| | | | |
|---|---|---|---|
| 2,627,859 | 2/1953 | Hargrave | 604/394 |
| 2,801,632 | 8/1957 | Burner et al. | 604/392 |
| 2,808,831 | 10/1957 | Winslett | 604/392 |
| 2,833,282 | 5/1958 | Moore | 604/386 |
| 2,910,982 | 11/1959 | Woodward | 604/392 |
| 3,150,664 | 7/1964 | Noel | 604/391 |
| 3,618,608 | 11/1971 | Brink | 604/391 |
| 3,827,107 | 8/1974 | Moore | 128/DIG. 15 |
| 3,882,870 | 5/1975 | Hathaway | 604/392 |
| 4,402,690 | 9/1983 | Redfern | 604/391 |
| 4,410,327 | 10/1983 | Baggaley | 604/391 |

Primary Examiner—C. Fred Rosenbaum
Assistant Examiner—Denise Whelton
Attorney, Agent, or Firm—Bull, Housser & Tupper

[57] ABSTRACT

An adjustable diaper has a generally rectangular body portion of a flexible, sheet-like material. The diaper has a front part with two pairs of openings which are elongated in the direction parallel to the sides of the body portion. The openings of each pair are near one side of the body portion and are the same distance from the one side. The openings of each pair are spaced-apart in a direction extending from the front end of the body portion so the openings coincide when the body portion is folded parallel to the front end between the openings of each said pair. A pair of strap members extend from each side of the body portion near the back end and include hook and loop fasteners for releasably securing each strap member to the back part of the body portion when each strap member extends through at least one of the openings and is doubled back to the back part of the body portion.

2 Claims, 6 Drawing Figures

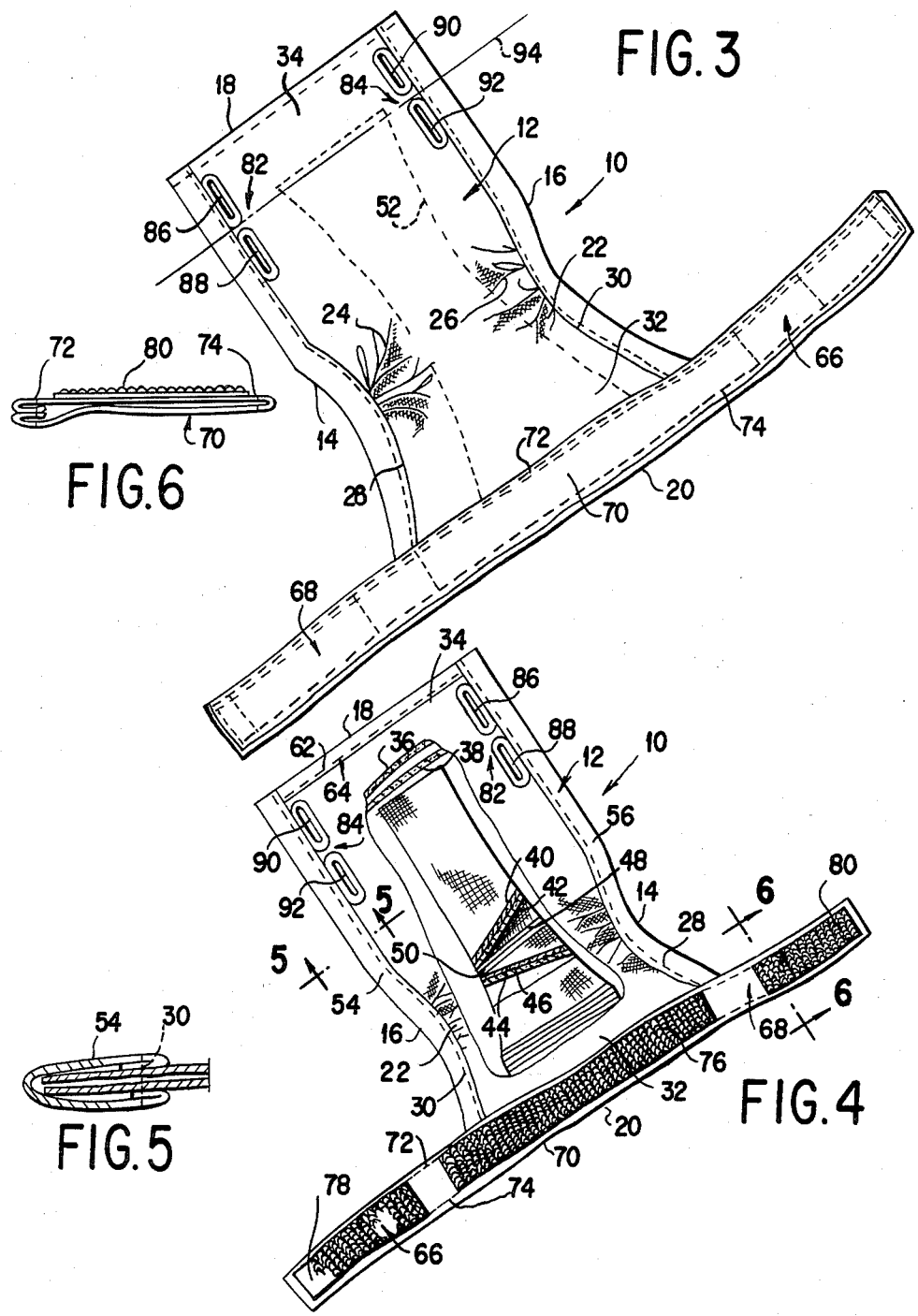

ADJUSTABLE DIAPER

BACKGROUND OF THE INVENTION

This invention relates to an adjustable, fitted diaper. The common cloth diaper is a simple piece of cloth folded in one of a number of ways so it can be drawn up between the legs of an infant and fastened about his waist with pins. The method is time consuming and requires the use of pins which could hurt the child when being pushed through the many layers of fabric. Attempts have been made to develop non-disposable diapers which are contoured to fit the child better. An example is found in Canadian Pat. No. 901,202 to Martin. This discloses a diaper which has a back wider than the front and a narrow middle portion for fitting the crotch area of the child. However, pins are still required to secure the diaper together. Another non-folding diaper of flannelette is disclosed in Canadian Pat. No. 372,540 to Caron where snap fasteners are used instead of pins.

Adjustable waist bands are used on the diaper disclosed in Canadian Pat. No. 943,702 to Brink and Canadian Pat. No. 376,028 to Lewis. Brink uses hook and loop type fasteners sold under the trade mark VELCRO. Such fasteners are also used on the diapers disclosed in Canadian Pat. No. 1,052,052 to Sonenstein.

Canadian Pat. No. 482,750 to Brink shows a diaper wherein a waistband passes through a slit.

Canadian Pat. No. 1,149,104 to Bolick discloses a diaper or the like which has straps connecting the front and the back. The straps extend through slits in both the front and the back. The slits are perpendicular to the parallel sides of the front and the back and a plurality of vertically spaced-apart slits are provided so the height of each strap can be adjusted. The straps are held at each end by buttons. Because of the orientation of the slits, the ends of the strap are held so they are not flat against the body of the infant. Instead, the edge of the strap is presented against the body at each end.

Accordingly, these earlier diapers have not provided a contoured, no-pin diaper capable of adjustment for different size infants which comfortably fits the infant and presents an attractive appearance. In Bolick for example, when lower slits are used for the straps, a considerable portion of material remains above the chosen slit presenting an untidy flap on both sides of the diaper.

SUMMARY OF THE INVENTION

According to the invention, there is an adjustable diaper with a generally rectangular body portion of a flexible, sheet-like material having opposite sides, a back end and a front end. The body portion has a relatively narrow central part for fitting under the crotch of an infant. There is a front part adjacent the front end for fitting about the front of the infant and a back part adjacent the back end for fitting about the back of the infant. The front part has two pairs of openings which are elongated in a direction parallel to the sides. The openings of each pair are near one side of the body portion, being the same distance from the one side and being spacedapart in a direction parallel to the sides. The openings of each pair coincide when the body portion is folded between the openings of each pair of openings. A pair of strap members extend from the sides of the body portion near the back end. Hook and loop type fasteners releasably secure each strap member to the back part of the body portion when each strap member extends through at least one of the openings and is doubled back to the back part of the body portion.

BRIEF DESCRIPTION OF THE DRAWINGS

In the drawings:

FIG. 3 is a plan view showing the inside of the diaper;

FIG. 4 is a plan view, partly broken away, showing the outside of the diaper and internal components;

FIG. 5 is an enlarged sectional view taken along line 5—5 of FIG. 4; and

FIG. 6 is an enlarged sectional view taken along line 6—6 of FIG. 4.

DESCRIPTION OF THE PREFERRED EMBODIMENTS

Figure 1:
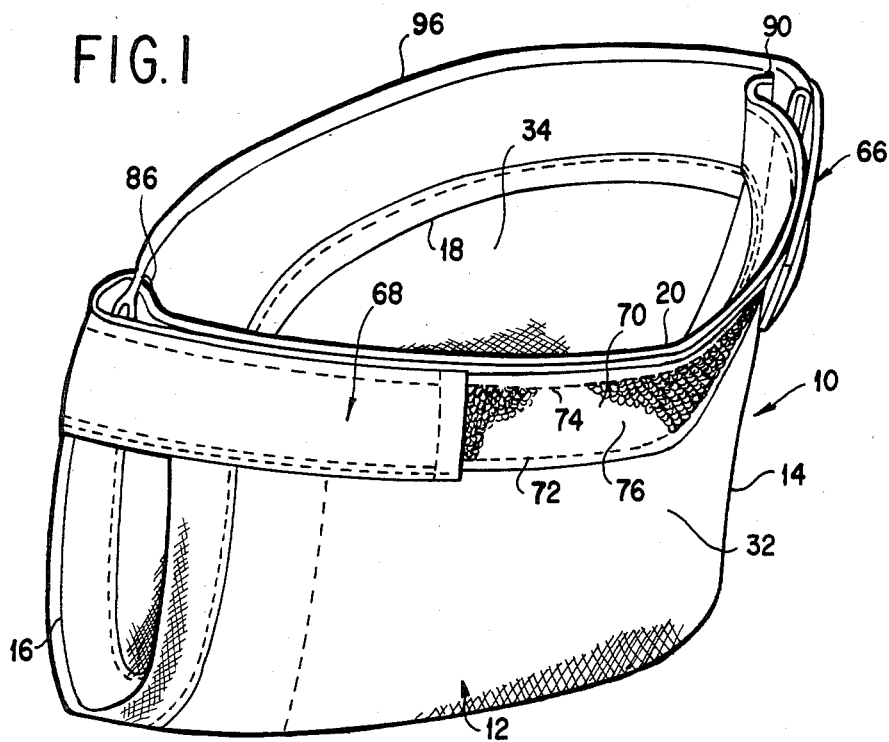
FIG. 1 is a perspective view of a diaper according to the invention shown adjusted in height for smaller infants.

Referring to the drawings, these illustrate an adjustable diaper 10 which includes a body portion 12 which, as seen in the unfolded positions of FIG. 3 and FIG. 4, is generally rectangular having opposite sides 14 and 16, a front end 18 and a back end 20. It may be observed that the body portion is wider adjacent back end 20 than near front end 18.

The body portion has a relatively narrow central portion 22 formed by gathers 24 and 26 prior to stitching at 28 and 30 near the sides 14 and 16. This produces a concave interior for a better fit. The body portion also has a front part 34 generally adjacent front end 18 and a back part 32 generally adjacent back end 20.

The body portion is made of a flexible sheet-like material, preferably cotton flannelette. Two layers of fabric 36 and 38 are used as seen in FIG. 4. Internally, additional somewhat trapezoidal-shaped layers of fabric are used for absorbency purposes. These are sandwiched together as seen in FIG. 4. The outer layers 40, 42, 44 and 46 extend from the central portion 22 into the back part 32 and the front part 34. Two additional layers 48 and 50 occur between layers 42 and 44 and extend from the central portion into the front part. The layers 40–50 are held in position between layers 36 and 38 by stitching 52 shown in FIG. 3.

The sides of the body portion are finished by cloth strips 54 and 56 folded over the edges and sewn in place by stitching 30 and 28 shown in FIG. 4. The use of gathers 24 and 26 in combination with cloth strips 54 and 56 and stitching 30 and 28 provides a more comfortable fit than the elastic portions used in prior art fitted diapers. FIG. 5 shows strip 54 in section. At front end 18 layer of cloth 38 is folded over to form a portion 62 ovelaying layer 36 and held in position by stitching 64.

At back end 20 the diaper has a pair of strap members 66 and 68 which form outer extensions of a waist band 70. As seen best in FIGS. 3, 4 and 6, the waist band 70 is formed of a single strip of cloth folded and with stitching 72 and 74 extending along opposite sides thereof.

Hook and look type fasteners, such as those sold under the trademark Velcro, are stitched to the outside of waist band 70 by the stitching 72 and 74 as well as additional stitching at the ends of the fastener portions. An elongated fastener portion 76 is stitched to the waist band 70 so it extends approximately from one side 16 of the body portion to the other side 14. This fastener portion in the preferred embodiment is the softer portion having loops of fibre because parts of this fastener portions are outwardly exposed. Fastener portions 78 and 80 are stitched to strap members 66 and 68, respectively, as shown in FIG. 4. These portions are adapted to engage with fastener portion 76 and are of the type comprising relatively stiff fibre hooks.

Two pairs 82 and 84 of openings are formed on the body portion near front end 18. These openings in the preferred embodiment are in the form of elongated slits surrounded by stitching similar to buttonholes. Pair 82 includes openings 86 and 88 which are near side 14, while pair 84 includes openings 90 and 92 near side 16. It should be noted that openings 86 and 88 are the same distance from side 14, while openings 90 and 92 are the same distance from side 16. It should also be noted that the openings are elongated in a direction parallel to the adjacent portions of sides 14 and 16 which are parallel near front 18. Opening 86 is spaced the same distance from front end 18 as is opening 90, while opening 88 is spaced the same distance from front end 18 as is opening 92. Furthermore, opening 86 is spaced-apart from opening 88, while opening 90 is spaced-apart from opening 92 the same distance. Thus, the openings coincide when the body portion is folded along line 94, shown in FIG. 3, to form a fold 96, as shown in FIG. 1. This Figure shows how the diaper is shaped and fitted to a smaller infant. From the flattened position shown in FIG. 3, the body portion is brought up along the front and back of the child. Strap member 66 is inserted through aperture 90 as shown in FIG. 1 and through aperture 92 which is immediately behind aperture 90. The strap member is then doubled back on itself so that fastener portion 78 engages fastener portion 76. Similarly, strap member 68 is inserted through apertures 86 and 88 and doubled back so fastener portion 80 mates with fastener portion 76. The fastener portions are adjusted so the diaper fits snugly around the waist of the infant. In this position the doubling of the diaper about fold 96 results in a lower profile to fit the smaller infant. At the same time, the position and orientation of the openings 86, 88, 90 and 92 allows the diaper to be folded to provide a neat and trim appearance without any unsightly flap and providing a great degree of comfort for the infant.

Figure 2:
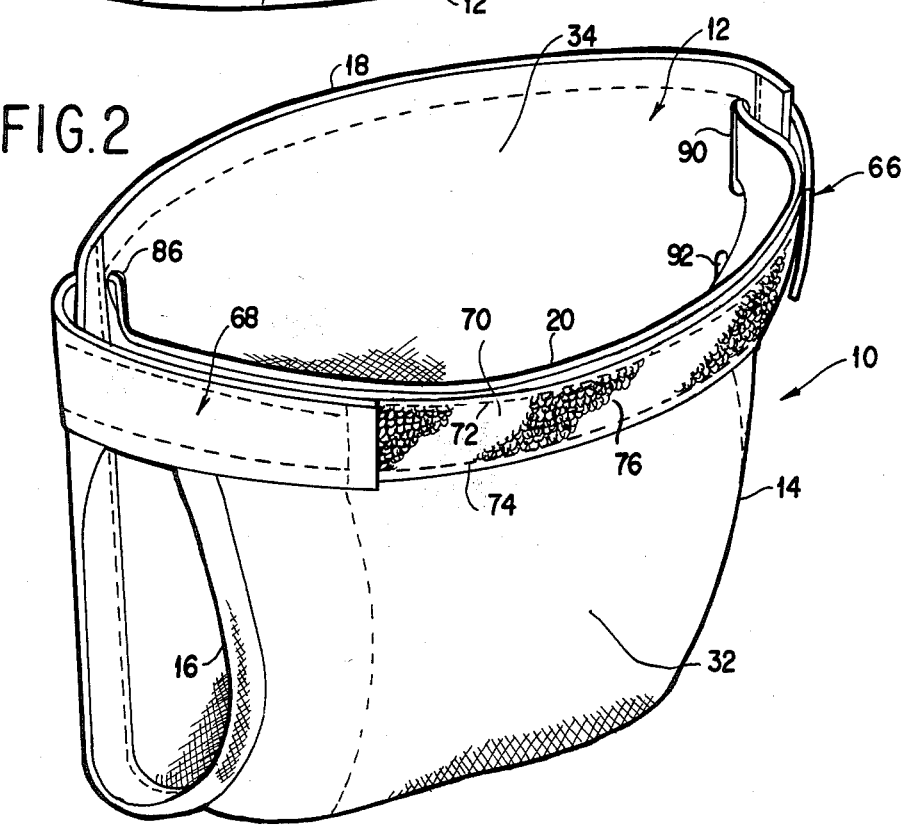
FIG. 2 is a perspective view similar to FIG. 1 showing the diaper adjusted in height for larger infants.

For larger infants, fold 96 is not made. Instead, strap members 66 and 68 are inserted only through openings 86 and 90. Openings 88 and 92 remain below openings 86 and 90. This can be seen for opening 92 in FIG. 2. Thus the profile of the diaper is higher to fit larger infants.

The orientations of openings 86, 88, 90 and 92 mean that the waist band 70, including strap members 66 and 68, are flat against the skin of the infant providing a comfortable fit. The use of fastener portions 76, 78 and 80 allows considerable adjustment of the diaper for infants having different waist sizes. The height of the diaper can also be varied by optionally folding the diaper along fold 96 as shown in FIG. 1.

As illustrated in the preferred embodiment, the fasteners should be at the back of the diaper to inhibit tampering by the infant.

What is claimed is:

1. An adjustable diaper comprising:

a generally rectangular body portion of two layers of a flexible, sheet-like material having opposite sides, a back end, a front end, the back end being wider than the front end, a central part for fitting under the crotch of the infant, a front part adjacent the front end for fitting about the front of the infant, the sides being parallel near the front end, and a back part adjacent the back end for fitting about the back of the infant, the central part having non-elastic gathers formed along the sides of the body portion and secured by stitching extending along the sides of the body portion, making the central part concave and narrower than the front part and the back part, the front part having two pairs of slot-like openings which extend lengthwise in a direction parallel to the sides, the openings of said each pair being near opposite sides of the body portion, the openings of each pair being spaced apart the same amount so the openings of said each pair coincide when the body portion is folded parallel to the front end between the openings of said each pair of openings;

a pluraliy of layers of moisture absorbent material between the layers of material of the body portion and sewn thereto;

a pair of strap members extending from said sides of the body portion near the back end;

the strap members being relatively thin and each having a width slightly less than the length of each said slot-like openings and being sufficiently long to extend through the slot-like openings of the front part and double back to overlie the back part;

and hook and loop-type fastener means on the straps and the back part for releasably securing each said strap member to the back part of the body portion when the straps are doubled back, the fastener means having hook portions on sides of the straps which face inwardly when the straps are doubled back.

2. A diaper as claimed in claim 1, wherein there are cloth strips folded over the sides of the body portion and secured thereto by stitching.

* * * * *